United States Patent [19]

Knotts

[11] Patent Number: 4,970,904
[45] Date of Patent: Nov. 20, 1990

[54] REVERSIBLE ADAPTOR AND GAS ANALYZER FOR TIRES

[75] Inventor: John M. Knotts, Norton, England

[73] Assignee: Newbow Engineering Industries Limited, Worcestershire, England

[21] Appl. No.: 353,470

[22] Filed: May 18, 1989

[30] Foreign Application Priority Data

May 18, 1988 [GB] United Kingdom ............... 8811859

[51] Int. Cl.$^5$ .......................................... G01N 1/00
[52] U.S. Cl. ................................. 73/863.86; 137/231
[58] Field of Search .............. 73/866.5, 864.81, 756, 73/863.86; 137/231, 270; 285/12, 93, 177

[56] References Cited

U.S. PATENT DOCUMENTS

| | | | |
|---|---|---|---|
| 1,357,153 | 10/1920 | Dicken | 285/12 |
| 3,115,033 | 12/1963 | Blowers | 73/756 |
| 4,345,783 | 8/1982 | Bergstrand | 285/12 |

FOREIGN PATENT DOCUMENTS 1147654 11/1957 France ......................... 285/177

Primary Examiner—Robert Raevis
Attorney, Agent, or Firm—Larson and Taylor

[57] ABSTRACT

A reversible adapter for connecting a tire pressure gauge or similar equipment to the inflation valve of a pneumatic type comprises a tubular body having a spigot at each end for selective connection to the gauge wherein each spigot is adapted for connection to a respective one of two different valve sizes such that the gauge may be connected to either valve by reversing the spigot connections to present the matching spigot for connection to the valve. A gas analyzer for connection to the inflation valve of a pneumatic tire to determine the oxygen content of the inflation gas is also described.

10 Claims, 3 Drawing Sheets

4,970,904

REVERSIBLE ADAPTOR AND GAS ANALYZER FOR TIRES

BACKGROUND OF THE INVENTION

This invention relates to adaptors for valves and in particular, though not exclusively to adaptors for connecting equipment to the inflation valve of pneumatic tires, and to a gas analyzer for testing the oxygen content of the inflation gas of pneumatic tires. As used herein the term "pneumatic" includes air and other elastic fluid(s) and gas(es).

Pneumatic tires are normally mounted on a wheel rim and are inflated by connecting an inflation valve to a suitable source of compressed air or other suitable elastic fluid(s) or gas(es).

The inflation valve also permits connection of a tire pressure gauge to test the inflation pressure as well as other test equipment as commonly used.

Previously, it has been necessary to provide a range of adaptors for connecting the equipment to different valve sizes commonly encountered in use. This is inconvenient as the user must change the adaptor for each different valve size and the adaptors are easily misplaced or lost.

SUMMARY OF THE INVENTION

The present invention is intended to remedy the disadvantage aforementioned. It solves the problem of providing a separate adaptor for each valve size by the provision of a reversible adaptor for selective connection to either one of two different valve sizes.

In its simplest form the adaptor comprises a tubular element of which each end has an inner portion and an outer portion with the inner portions being adapted for connection to a respective one of two valve sizes and the outer portions being adapted for connection to equipment to be connected to the valve.

The invented adaptor enables equipment such as a tire pressure gauge, tire inflation means or the like to be connected to either one of two different valve sizes by connecting the adaptor to the equipment so as to present the inner end portion of the appropriate size for connection to the valve.

By this simple expedient of the invented, reversible adaptor, a single adaptor may be used where previously two separate adaptors have been required with consequential convenience and cost savings to the user.

Pneumatic tires are normally inflated with atmospheric air which consists essentially of oxygen and nitrogen in the amounts of 20.99% oxygen and 78.03% nitrogen by volume, i.e. a ratio of approximately 1:4 by volume.

It has now been found that overheating of pneumatic tires can result in decomposition of the tire materials to produce a gas which, when mixed with the normal oxygen content of inflation air under pressure, creates an explosive mixture. Such overheating can be caused by a number of factors including high loads, and/or speeds, incorrect inflation pressure, and brake malfunction.

Airplane tires are particularly susceptible to overheating in service and it is now a mandatory requirement in certain countries for airplane tires to be inflated with dry nitrogen having a maximum oxygen content of 5% to prevent creation of such explosive mixture.

According to another aspect, the present invention provides a device for testing pneumatic tires to determine the oxygen content of the inflation gas, in particular the oxygen content of the inflation gas of airplane tires, whereby an oxygen content sufficient to give rise to a risk of an explosion occurring may be detected and rectified.

In its simplest form the device comprises connector means for operative engagement with a tire valve to open the valve and release the inflation gas into the device, sensor means for detecting the oxygen content of the gas, and display means responsive to an output signal generated by the sensor means to provide an indication of the oxygen content.

The invented device enables the oxygen content of the inflation gas of airplane tires to be checked during the normal pre-flight tests so that an oxygen content above a safe level, for example the 5% now mandatory in certain countries, can be detected and rectified before take-off.

In this way the risk of a tire exploding in flight which could result in damage sufficient to cause the airplane to crash and which, in any event, would make landing difficult and hazardous is considerably reduced.

The sensor means is preferably calibrated against atmospheric air having known oxygen concentration before and/or after testing the tire inflation gas. For example, by passing atmospheric air through the device by a motor driven fan housed within the device. In this way, errors or inaccuracies in the readings obtained are avoided.

Exemplary embodiments of the invented reversible adaptor and gas analyzer device will now be described in more detail, by way of example only, with reference to the accompanying drawings.

DETAILED DESCRIPTION OF THE EXEMPLARY EMBODIMENTS

Airplane tires are commonly provided with one of two different valve sizes with the result that, when connecting equipment to the tires such as a tire pressure gauge or a source of inflation gas(es), the user has previously always had to select and fit an appropriately sized adaptor according to the size of the valve.

Figure 1:
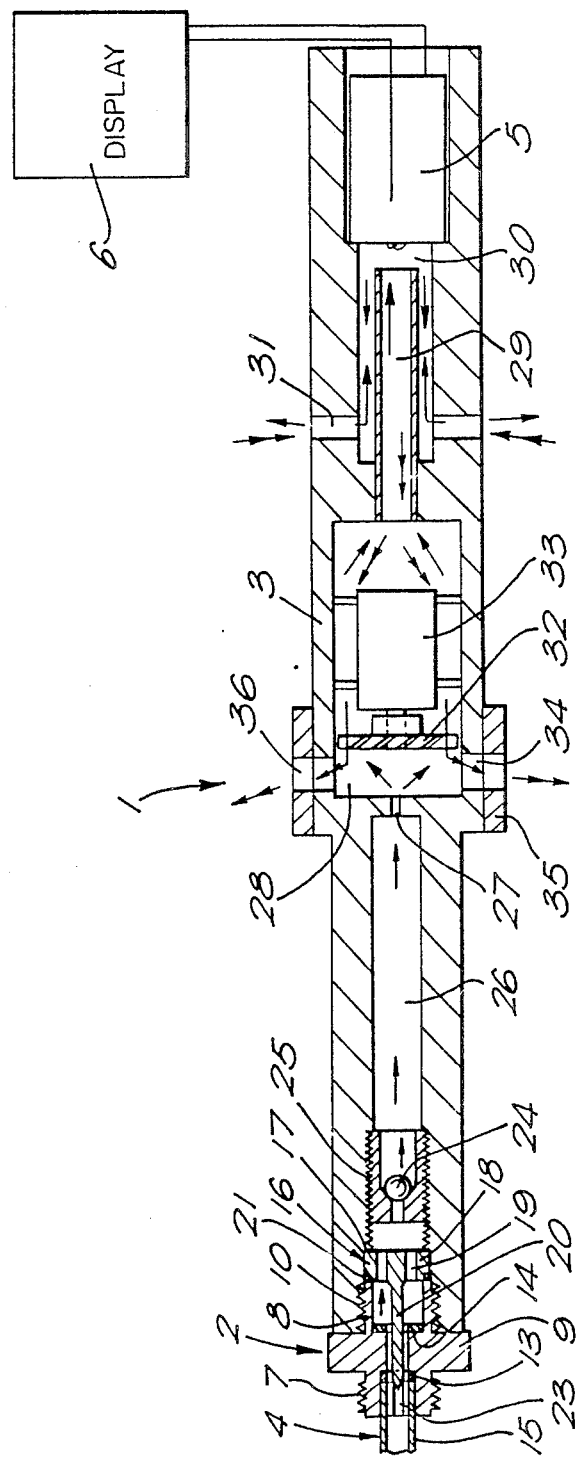
FIG. 1 shows in longitudinal section a gas analyzer for testing the oxygen content of the inflation gas of a pneumatic tire connected to an inflation valve of the tire by a reversible adaptor.

FIG. 1 shows a portable gas analyzer 1 for testing the oxygen content of airplane tires and a reversible adaptor 2 for selectively connecting the analyzer 1 to either one of the two different valve sizes. In this way the problems and disadvantages of providing and fitting separate adaptors for each valve size as previously required when connecting equipment to different valve sizes is avoided.

The analyzer 1 has a tubular body 3 with the adaptor 2 releasably secured at one end for connection to a valve 4 of a tire (not shown) to be tested. The other end of the body 3 is provided with an oxygen sensor 5 for detecting the oxygen content of the inflation gas and is connected to display means 6 for providing a read-out of the content. The display means 6 may provide a digital or analog display of the oxygen concentration. In addition to or in place of such display, the analyzer 1 may provide a visual and/or audio warning of whether the oxygen concentration is inside or outside safe limits, for example by appropriate warning lights or buzzers, as desired.

Figure 2:
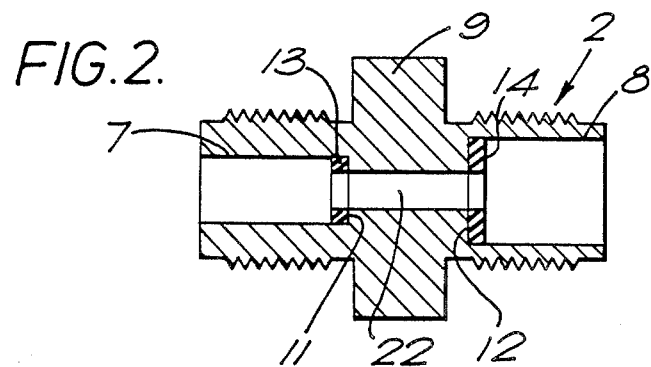
FIG. 2 shows in longitudinal section, to an enlarged scale, the reversible adaptor shown in FIG. 1.

As best shown in FIG. 2, the adaptor 2 comprises a tubular element the end portions of which form spigots 7,8 for selective connection to the analyzer 1 and valve 4. Intermediate the ends, the adaptor 2 has an external annular collar 9 which provides a grip for the user to facilitate mounting of the adaptor 2 in the end of the body 3.

The spigots 7,8 are of different internal diameter for receiving a respective one of two different valve sizes and of the same external diameter provided with external screw threads for selective engagement with an end portion 10 of the body 3 provided with a complementary internal screw thread by means of which the adaptor 2 is releasably secured.

By this arrangement, the adaptor 2 is reversible for connecting the analyzer 1 to each of two different valve sizes corresponding to the internal diameters of the spigots 7,8 as desired.

The spigots 7,8 are formed with respective internal annular abutment shoulders 11,12 providing seatings for annular sealing rings 13,14 which ensure an air-tight seal with the stem 15 of the valve 4 received in the matching spigot 7,8.

A valve actuator comprising a probe 16 is seated against an abutment shoulder 17 in the end of the body 3 and is retained by the inner end of the adaptor 2 screwed into the body 3.

The probe 16 has a head 18 formed with a plurality of circumferentially spaced axially extending holes 19 and a central axially extending shank 20.

The head 18 is sealed relative to the inner end of the adaptor 2 by a sealing ring 21 and the shank 20 extends with radial clearance through a central bore portion 22 connecting the spigots 7,8 into the outer end of the adaptor 2 for co-operating with the valve 4 in both fitted positions of the adaptor 2.

The adaptor 2 is a push-fit on the valve stem 15 and the probe shank 20 engages and depresses the valve core 23 to open the valve 4 and release the inflation gas which passes through the adaptor 2 and the holes 19 in the probe head 18 and is admitted through a non-return ball valve 24 screwed into a threaded bore portion 25 of the body 3 to a sample chamber 26 within the body 3.

From the sample chamber 26, the inflation gas passes through a snubber orifice 27 which reduces the pressure into an intermediate chamber 28 from where it passes through tube 29 into a detection chamber 30 and is directed past the oxygen sensor 5 before exiting from the analyzer 1 through radial ports 31.

The oxygen sensor 5 produces a signal related to the concentration of oxygen in the inflation gas and this signal is modified and/or amplified electronically to produce a digital or analog read-out at the display means 6 indicating the proportion of oxygen in the inflation gas.

To reduce errors or inaccuracies in the readings obtained, the sensor 5 is calibrated before and/or after testing by passing atmospheric air having a known oxygen content of 20.99% by volume through the analyzer 1.

For such calibration, an aspirator unit comprising a fan 32 and an electric motor 33 therefor is mounted in the intermediate chamber 28 and is controlled by a manually operable sleeve valve 35 externally mounted on the body 3.

The valve 35 is rotatable to align a series of circumferentially spaced apart apertures 36 with radial orifices 34 leading from the intermediate chamber 28 to start the motor 33 which drives the fan 32 causing atmospheric air to be drawn into the analyzer 1 through the ports 31 past the sensor 5 in the detection chamber 30 and into the intermediate chamber 28 from where it is expelled through the orifices 34.

For testing the inflation gas of a tire as above-described, the orifices 34 are closed by rotating the sleeve valve 35 to move the apertures 36 out of registration with the orifices 34 and stop the motor 33.

As will be appreciated, the gas analyzer 1 enables the oxygen content of the inflation gas to be readily checked during routine pre-flight checks so that tires having an oxygen content sufficient to create an explosive mixture can be replaced thereby providing improved safety.

Additionally, the adaptor 2 enables the analyzer 1 to be connected to either one of the two valve sizes commonly used for airplane tires thereby reducing the number of components with consequential cost savings and convenience to the user.

Although the analyzer 1 and adaptor 2 have been described with reference to airplane tires, it will be appreciated that they have application both in combination and separately to all types of pneumatic tires for airplanes, cars, lorries, off-the-road vehicles and the like including both tubeless tires in which the valve is mounted in the wheel rim and tires provided with an inner tube incorporating the valve.

Additionally, it will be understood that the adaptor and the modifications described later herein have application to the connection of all types of equipment to either one of two valve sizes of pneumatic tires as required. Thus, the adaptor has application to tire pressure gauges, tire inflation means and any other equipment such as the analyzer above-described as may be connected to tire valves for any purpose.

Figure 3:
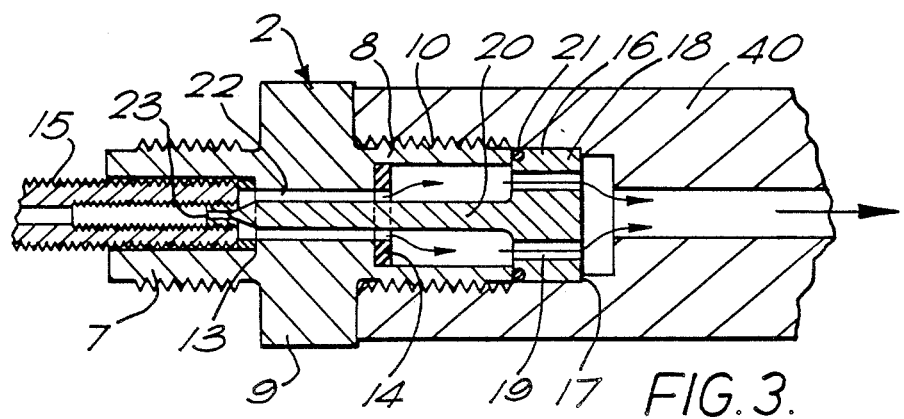
FIG. 3 shows in longitudinal section application of the reversible adaptor shown in FIG. 2 to a tire pressure gauge.

Referring now to FIG. 3, reference numeral 40 indicates a handstock of a tire pressure gauge (not shown) in which the reversible adaptor 2 and actuator probe 16 are mounted as described above with reference to FIGS. 1 and 2 and like reference numerals are used to indicate corresponding parts.

In this alternative application of the adaptor 2 to a tire pressure gauge, the adaptor 2 is reversible to connect the gauge to either one of two valve sizes as desired and the probe 16 is arranged to open the valve in either fitted position of the adaptor 2 to admit the inflation gas to the gauge in similar manner to that described with reference to FIGS. 1 and 2 and will be understood by those skilled in the art without further description.

Figure 4:
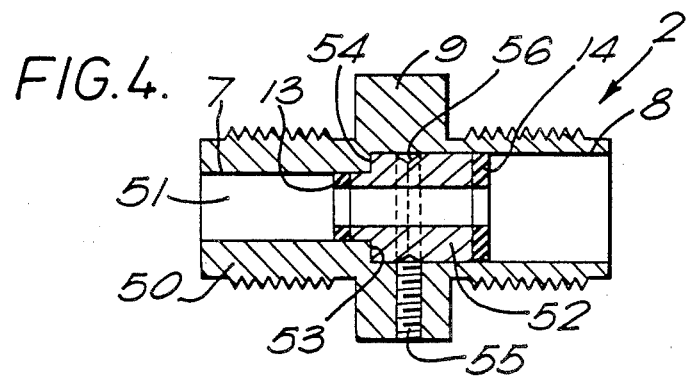
FIG. 4 shows in longitudinal section, a modification to the reversible adaptor shown in FIGS. 1 to 3.

Referring now to FIG. 4, a modification to the reversible adaptor 2 shown in FIGS. 1 to 3 is shown in which like reference numerals are used to indicate corresponding parts.

The adaptor 2 comprises a tubular outer body 50 having a stepped through bore 51 and a tubular insert 52 slidably received in the bore 51. The opposed ends of the insert 52 are of different external diameter corresponding to the internal diameter of the spigots 7,8 forming an annular abutment shoulder 53 which seats against an annular abutment shoulder 54 formed at the junction of the spigots 7,8 to axially locate the insert 52 in the bore 51.

The sealing rings 13,14 are secured, for example bonded, to the opposed ends of the insert 52 and the insert 52 is releasably secured in the bore 51 by a transverse grub screw 55 mounted in the collar 9 and engaging an annular groove 56 of V-shape formed in the outer surface of the insert 52.

As will be appreciated, securing the sealing rings 13,14 to the insert 52 releasably secured in the adaptor bore 51 prevents accidental or inadvertent loss of the sealing rings 13,14 in service and facilitates replacement of one or both sealing rings 13,14 if required by simple removal and replacement of the insert 52.

In use, the adaptor 2 is reversible for connecting equipment to either one of two valve sizes as desired and retains an actuator probe for the valve as described previously herein.

Figure 5:
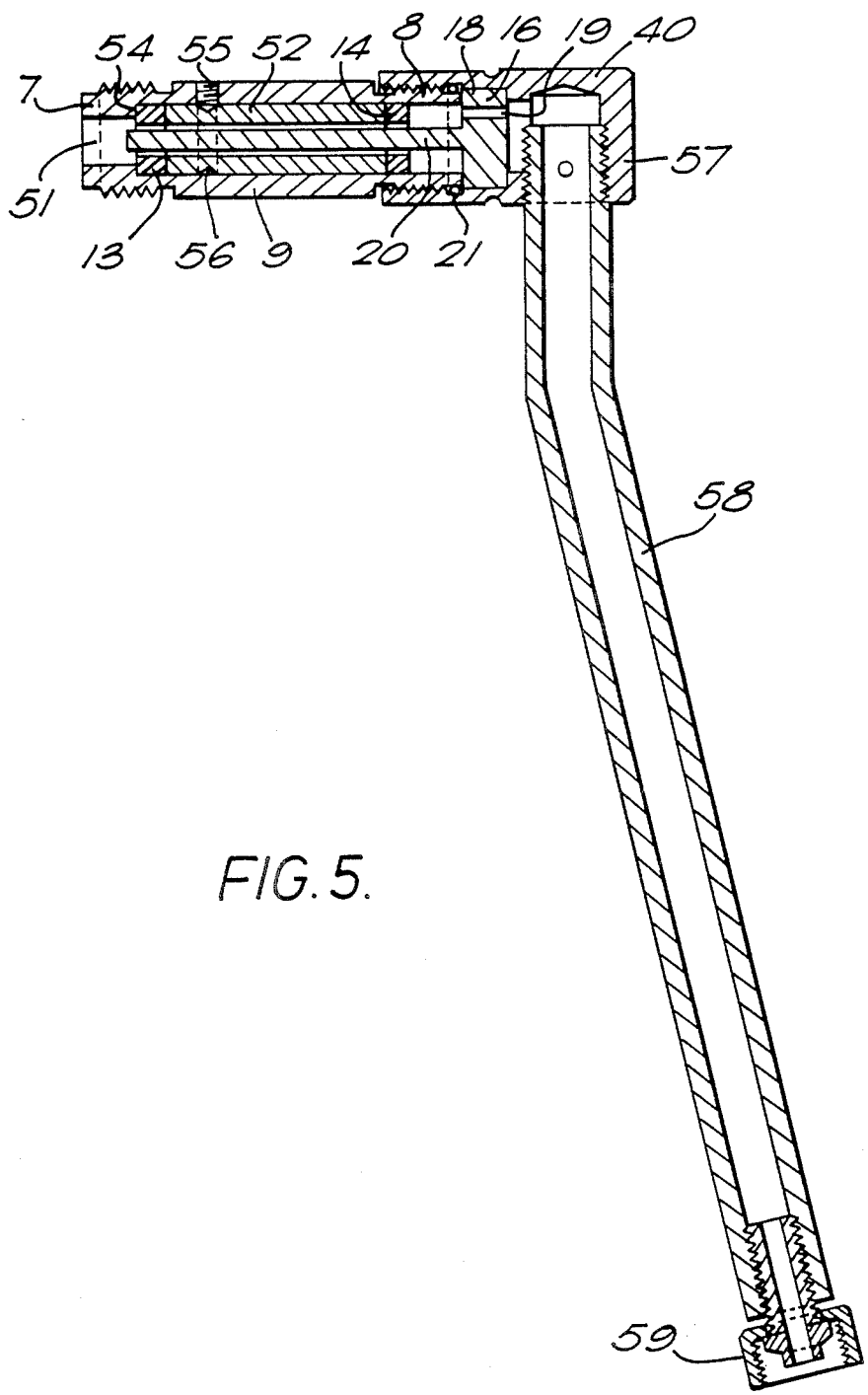
FIG. 5 snows in longitudinal section, a modification to the reversible adaptor shown in FIG. 4, the adaptor being shown mounted in a headstock of a tire pressure gauge.

Referring now to FIG. 5, a modification of the adaptor 2 shown in FIG. 4 is shown in which like reference numerals are used to indicate corresponding parts.

The outer body of the adaptor 2 has an elongated central portion and the insert 52 is of uniform diameter slidably received and retained in the wider end of the stepped bore 51 by grub screw 55 engaging groove 56.

Sealing ring 14 is secured to one end of the insert 52 and sealing ring 13, separate from the insert 52, is seated against and retained between the abutment shoulder 53 within the bore 51 and the other end of the insert 52. Alternatively, both sealing rings 13 and 14 could be secured to the insert 52.

The adaptor 2 is shown mounted with valve actuator probe 16 in a head 57 of the handstock 40 of a tire pressure gauge. The head 57 has a main bore of stepped profile in which the probe 16 is retained by screwing one end of the adaptor 2 into the end of the bore.

The probe shank 20 extends with radial clearance through the insert 52 to co-operate with a valve received in the outer end of the adaptor 2 and the probe head 18 has at least one through hole 19 for passage of the inflation medium as described previously herein.

Screwed into the head 57 at right angles to the main bore is a pipe 58 connected to the gauge by any suitable means indicated generally by reference numeral 59. The pipe 58 provides an extended reach and grip extending normal to longitudinal axis of the adaptor 2 for assisting the user in locating the adaptor 2 on the valve of a tire (not shown), particularly where access to the valve is restricted for any reason.

It will be understood that the adaptor is not limited to the exemplary embodiments above-described.

For example, to prevent the adaptor being blown-off the valve stem, the spigots may be internally threaded for engagement with an externally threaded portion of the valve stem. Alternatively any other suitable means may be used to provide a mechanical interlock between the adaptor and the valve stem.

The spigots may be adapted for releasable connection to the equipment by any suitable means.

The valve actuator probe may be replaced by any suitable means for co-operating with the valve when received in either spigot.

Similarly, it will be understood that the analyzer is not limited to the exemplary embodiment above-described. For example, the reversible adaptor may be replaced by any other suitable means for connecting the analyzer to a valve of a pneumatic tire to be tested.

Finally, it will be appreciated that the adaptor may be used to connected equipment to any pressurized body having a valve and is not limited to tire valves as described in the exemplary embodiments.

I claim:

1. An adaptor for connecting equipment to a valve of a pressurized body, the adaptor comprising a tubular element of which each end has an inner portion and an outer portion with said inner portions being adapted for connection to a respective one of two valves of different sizes and said outer portions being adapted for selective connection to the equipment such that the adaptor is reversible to enable selective connection of the equipment to either one of the two valves.

2. An adaptor according to claim 1 wherein said outer end portions are externally threaded for releasable connection to the equipment and said inner end portions are of different diameter for receiving by push-fit the corresponding valve.

3. An adaptor according to claim 1 wherein each inner end portion is provided with a respective sealing ring for sealing engagement with the valve.

4. An adaptor according to claim 3 wherein said sealing rings are arranged at opposite ends of a central bore portion extending between said inner end portions.

5. An adaptor according to claim 3 wherein said sealing rings are arranged at opposite ends of a tubular insert releasably secured within said tubular element between said inner end portions.

6. An adaptor according to claim 5 wherein said insert has at least one said sealing ring secured thereto.

7. An adaptor according to claim 1 comprising a valve actuator for actuating the valve connected to said adaptor.

8. An adaptor according to claim 7 wherein said valve actuator comprises a probe having a head and an axially extending shank, said head being arranged at one end of said adaptor remote from the valve and said shank extending longitudinally of said adaptor so as to co-operate with the valve connected to the other end of said adaptor.

9. An adaptor according to claim 8 wherein said adaptor and probe are adapted to be releasably secured to a handstock of the equipment.

10. An adaptor for connecting equipment to a valve of a pressurized body, said adaptor comprising a tubular element having a spigot at each end for selective connection to the equipment with each spigot being adapted for connection to a respective one of two valves of different sizes whereby said adaptor is reversible for connecting the equipment to either one of the two valves.

* * * * *